US010010682B2

(12) United States Patent
Adam

(10) Patent No.: US 10,010,682 B2
(45) Date of Patent: Jul. 3, 2018

(54) AUTO-RETRACTIBLE SYRINGE

(71) Applicant: Timothy John Adam, Kew VIC (AU)

(72) Inventor: Timothy John Adam, Kew VIC (AU)

(*) Notice: Subject to any disclaimer, the term of this patent is extended or adjusted under 35 U.S.C. 154(b) by 206 days.

(21) Appl. No.: 14/778,912

(22) PCT Filed: Mar. 25, 2014

(86) PCT No.: PCT/AU2014/000309
§ 371 (c)(1),
(2) Date: Sep. 21, 2015

(87) PCT Pub. No.: WO2014/153599
PCT Pub. Date: Oct. 2, 2014

(65) Prior Publication Data
US 2016/0045677 A1    Feb. 18, 2016

(30) Foreign Application Priority Data

Mar. 25, 2013 (AU) ................................ 2013901074

(51) Int. Cl.
*A61M 5/32* (2006.01)
*A61M 5/20* (2006.01)

(52) U.S. Cl.
CPC .......... *A61M 5/3234* (2013.01); *A61M 5/326* (2013.01); *A61M 2005/2073* (2013.01); *A61M 2005/3264* (2013.01)

(58) Field of Classification Search
CPC .. A61M 5/3234; A61M 5/3232; A61M 5/326; A61M 5/3257; A61M 5/20;
(Continued)

(56) References Cited

U.S. PATENT DOCUMENTS 4,737,144 A * 4/1988 Choksi ................ A61M 5/3243
604/198
4,767,413 A * 8/1988 Haber .................... A61M 5/326
604/198
(Continued)

FOREIGN PATENT DOCUMENTS

WO    2007/144507 A1    12/2007

OTHER PUBLICATIONS

Supplementary European Search Report dated Nov. 9, 2016 from corresponding Application No. EP 14776478.

*Primary Examiner* — Theodore Stigell
*Assistant Examiner* — Hong-Van Trinh
(74) *Attorney, Agent, or Firm* — Dilworth IP, LLC

(57) ABSTRACT

An auto-retracting hypodermic syringe has a housing extending axially to form a collar and housing interacting syringe components, an outer barrel is fixed within or forms part of the housing and an inner barrel is slidably mounted within the outer barrel for rearward movement within the outer barrel, the inner barrel has a mount for mounting a hypodermic needle on it or a needle already within a mount; a plunger has a piston on its distal end for withdrawing liquid dosage into the inner barrel when the plunger is pulled back and for injecting dosage when the plunger is pushed forward; axially-spaced, different-diameter discs on the plunger engage with radially pivoting, hinged latching arms formed on the proximal end of the housing and there are other associated latch members on the inner barrel and the housing which move inwards and outwards in correspondence with forward and rearward movements of the plunger; a coil spring is placed between the housing and inner barrel to exert needle retraction force against the inner barrel to retract it into the housing after completion of injection of syringe contents whereupon a latch locks it into the housing.

20 Claims, 20 Drawing Sheets

A-A

(58) Field of Classification Search
CPC .. A61M 2005/2073; A61M 2005/3264; A61M 2005/3238; A61M 5/3243; A61M 5/31501; A61M 5/5013; A61M 5/502
USPC .................................. 604/196, 110, 220, 223
See application file for complete search history.

(56) References Cited

U.S. PATENT DOCUMENTS

| | | | | |
|---|---|---|---|---|
| 4,787,891 | A * | 11/1988 | Levin | A61M 5/3287 604/136 |
| 5,106,379 | A * | 4/1992 | Leap | A61M 5/3271 604/198 |
| 5,181,909 | A * | 1/1993 | McFarlane | A61M 5/315 604/191 |
| 6,613,022 | B1 * | 9/2003 | Doyle | A61M 5/326 604/192 |
| 7,662,131 | B2 * | 2/2010 | Rimlinger | A61M 5/326 604/110 |
| 2004/0147875 | A1 * | 7/2004 | Wallace | A61M 5/31501 604/110 |
| 2006/0200077 | A1 | 9/2006 | Righi et al. | |
| 2007/0250003 | A1 * | 10/2007 | Bare | A61M 5/3234 604/110 |
| 2008/0262423 | A1 * | 10/2008 | Ingram | A61M 5/31501 604/110 |
| 2009/0204076 | A1 * | 8/2009 | Liversidge | A61M 5/31501 604/196 |
| 2010/0179487 | A1 * | 7/2010 | Woehr | A61M 5/31511 604/196 |
| 2015/0065955 | A1 * | 3/2015 | Ierfino | A61M 5/3232 604/110 |

* cited by examiner

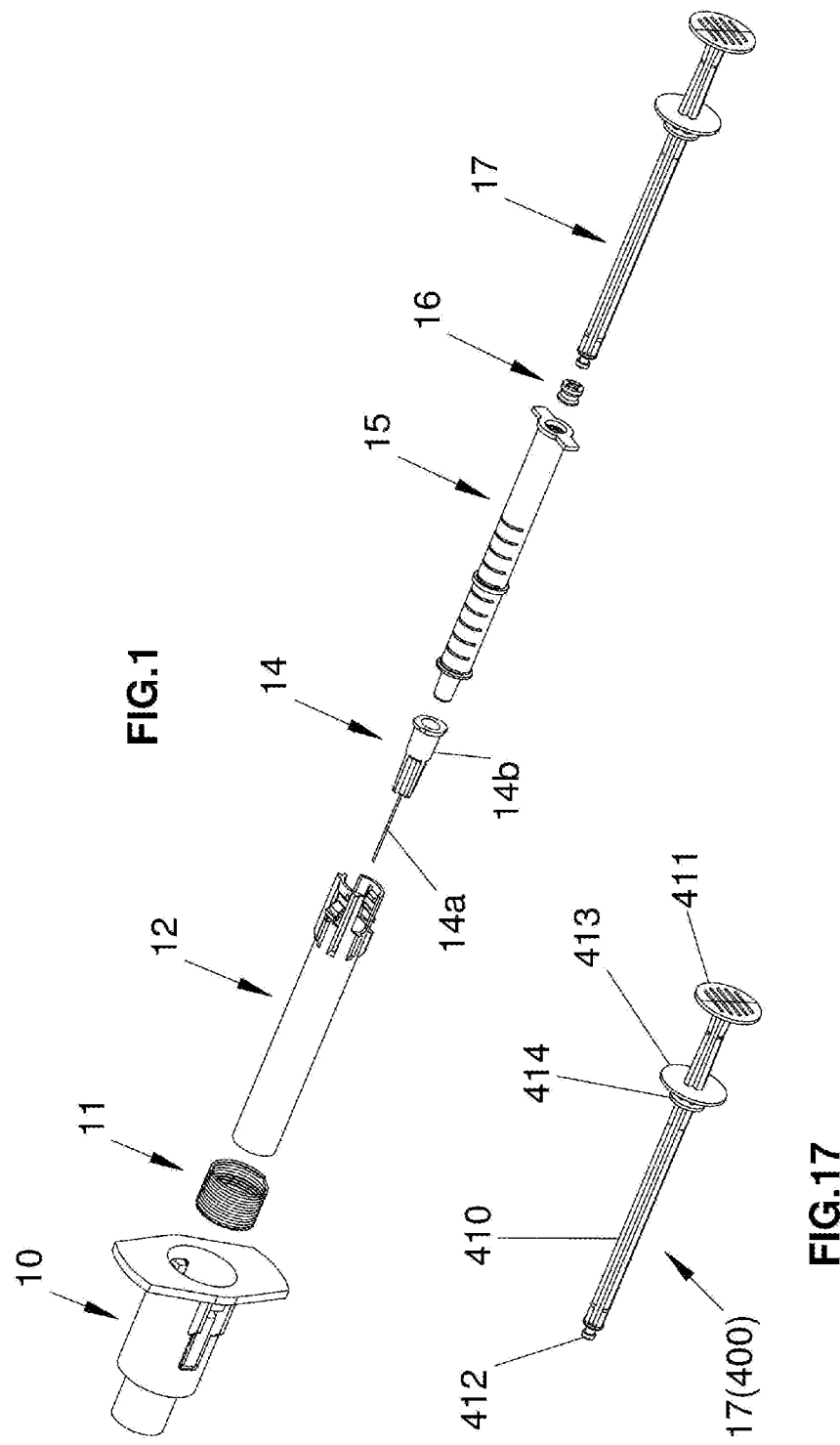

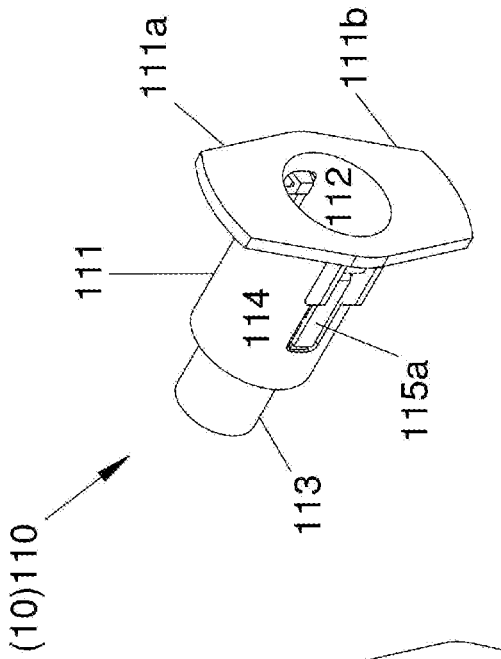
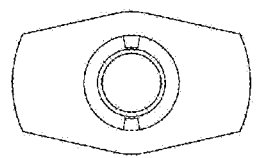
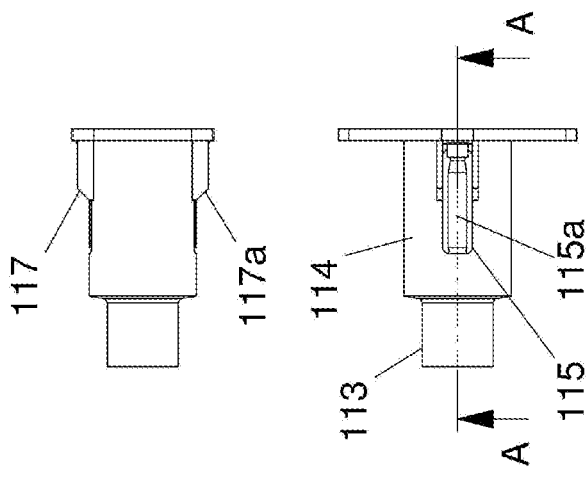
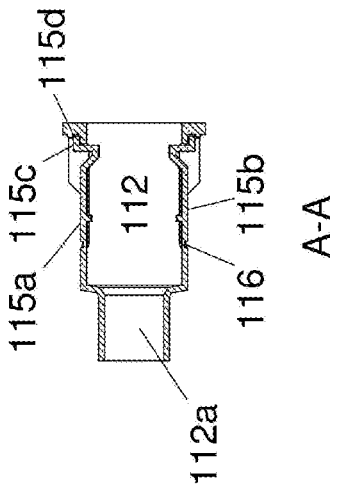

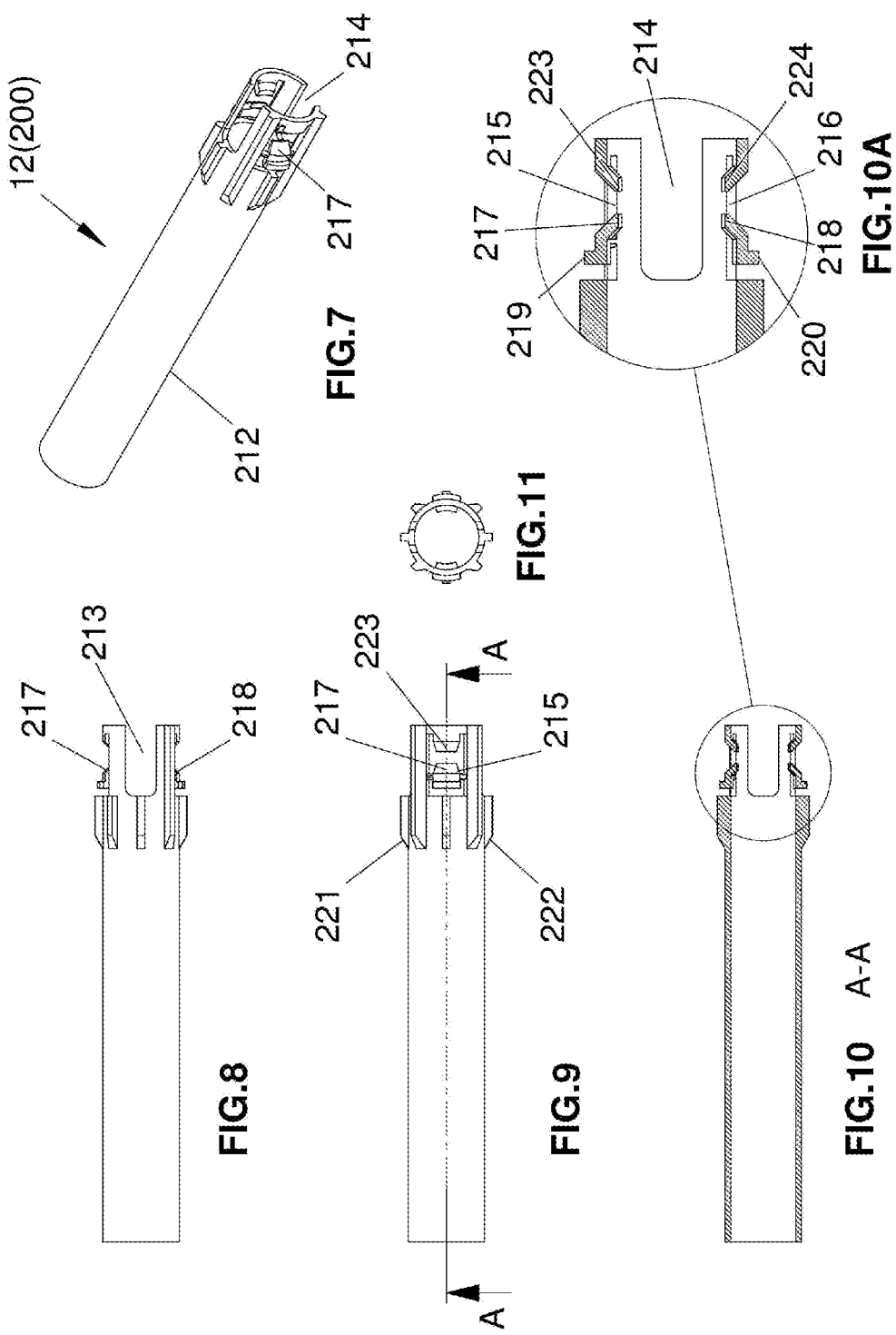

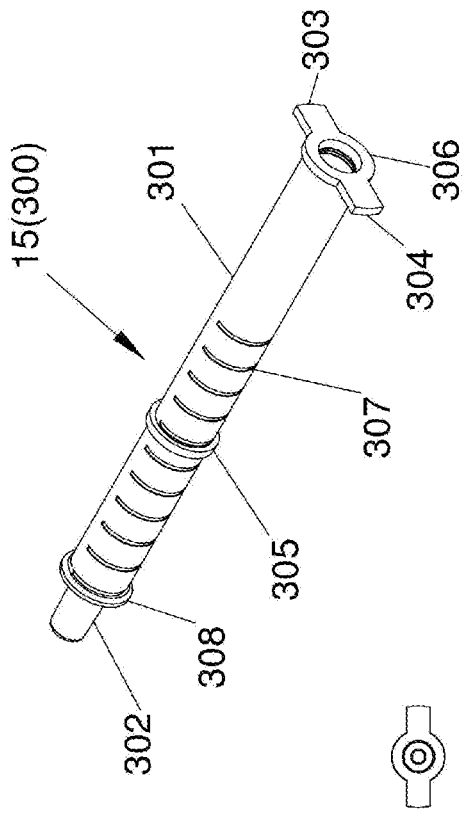
FIG.12
FIG.16
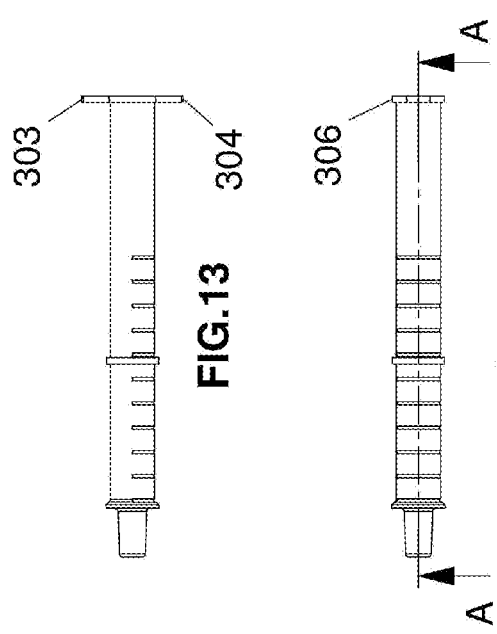
FIG.13
FIG.14
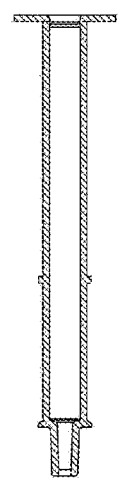
A-A
FIG.15

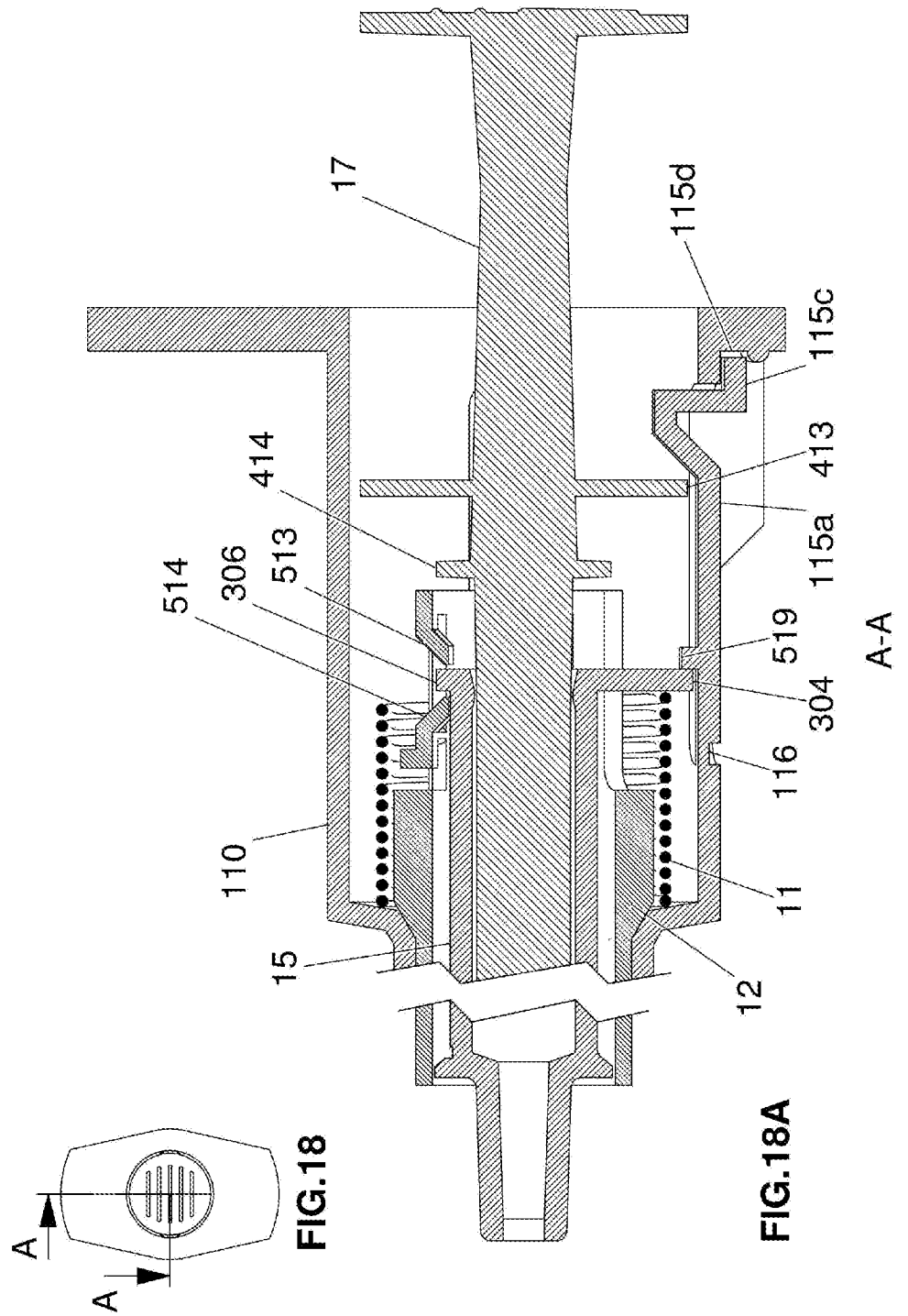

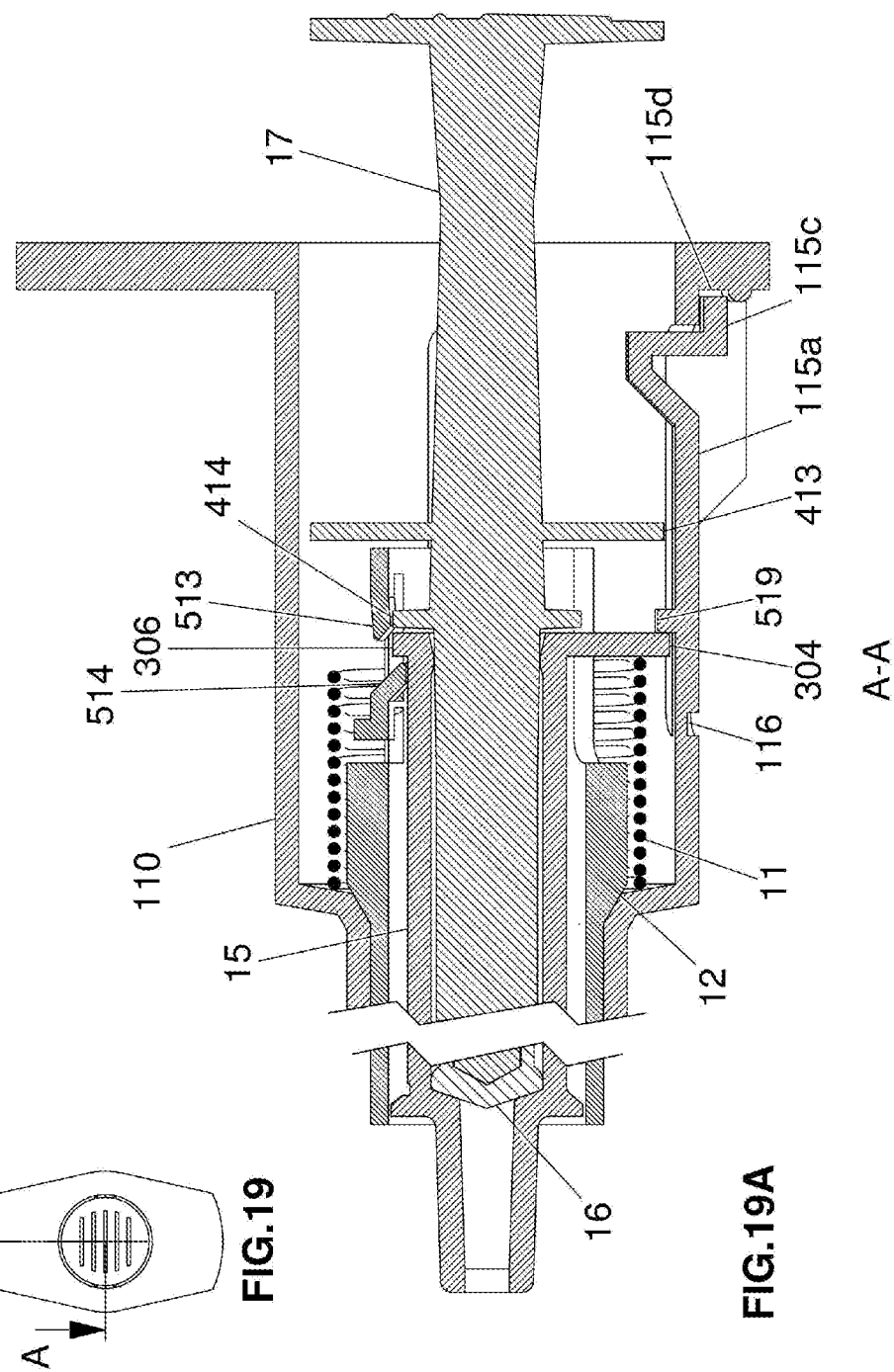

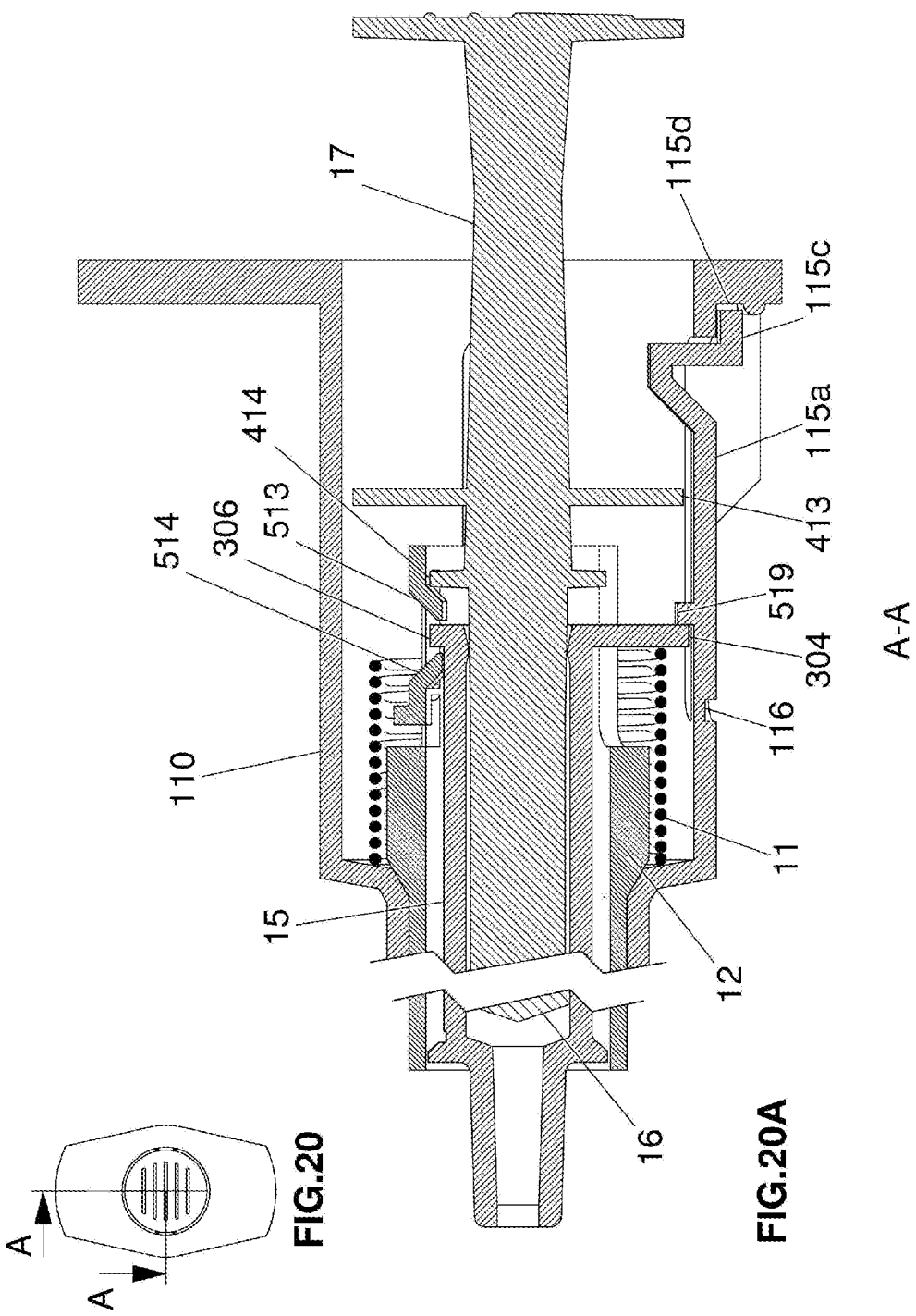

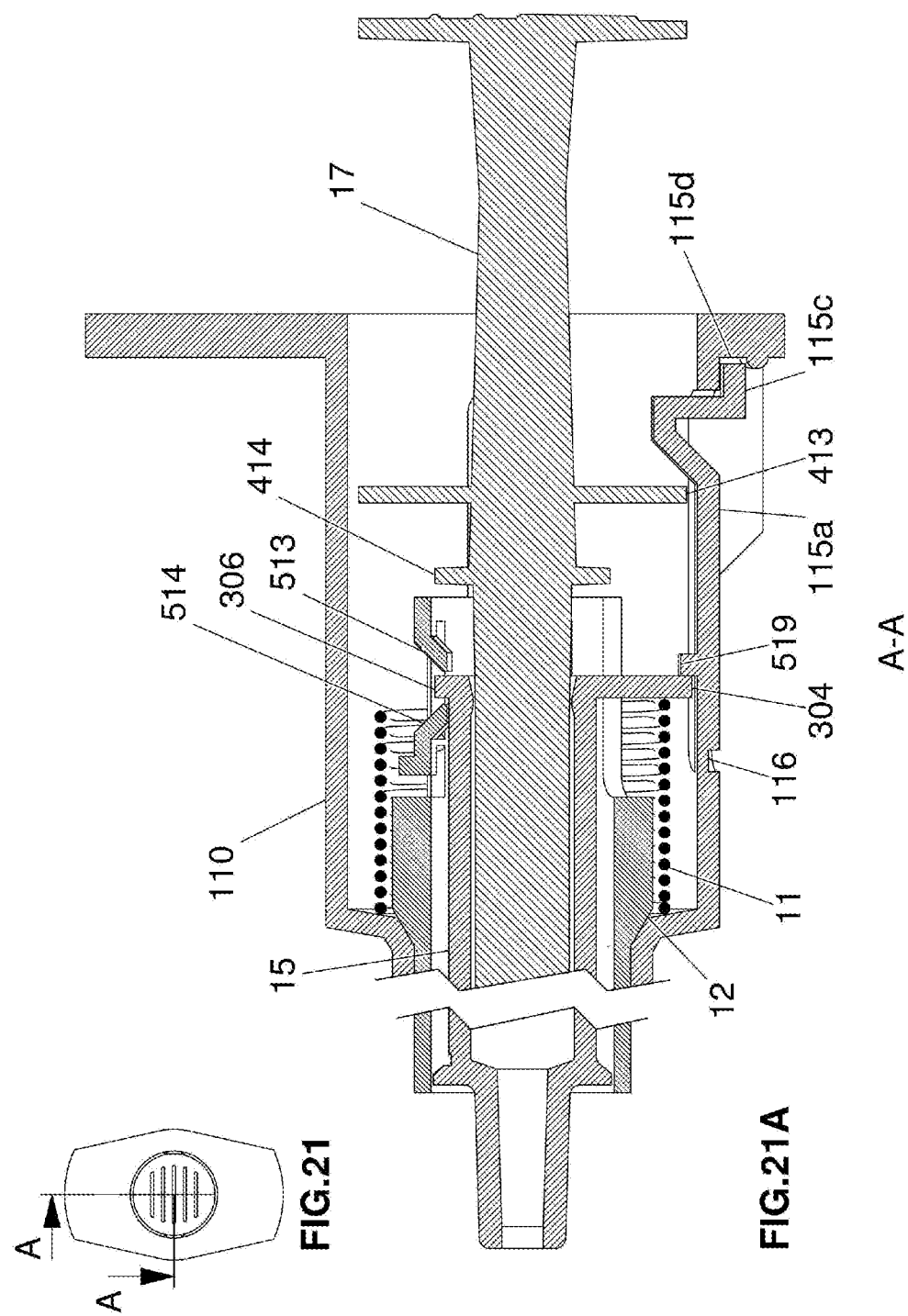

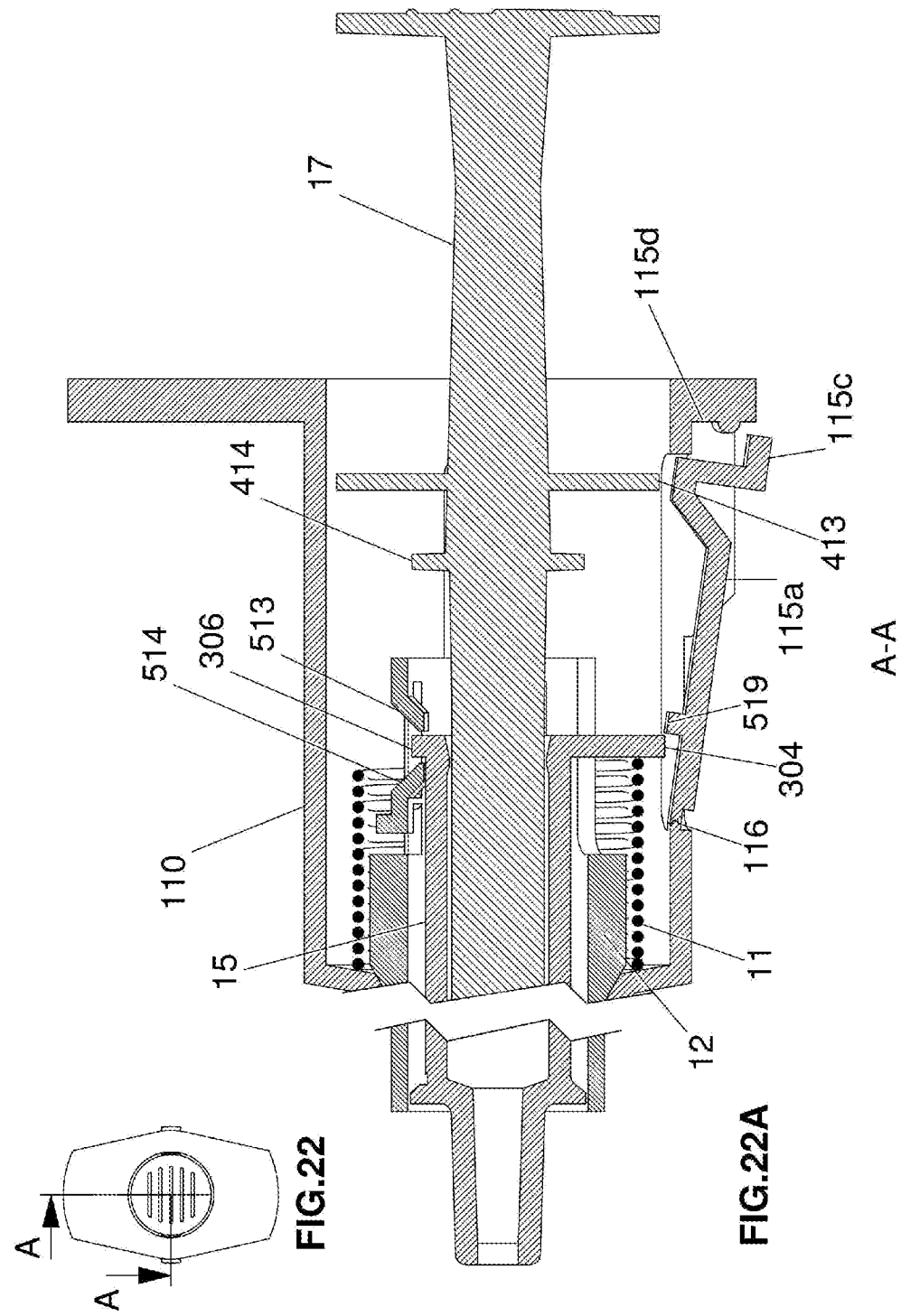

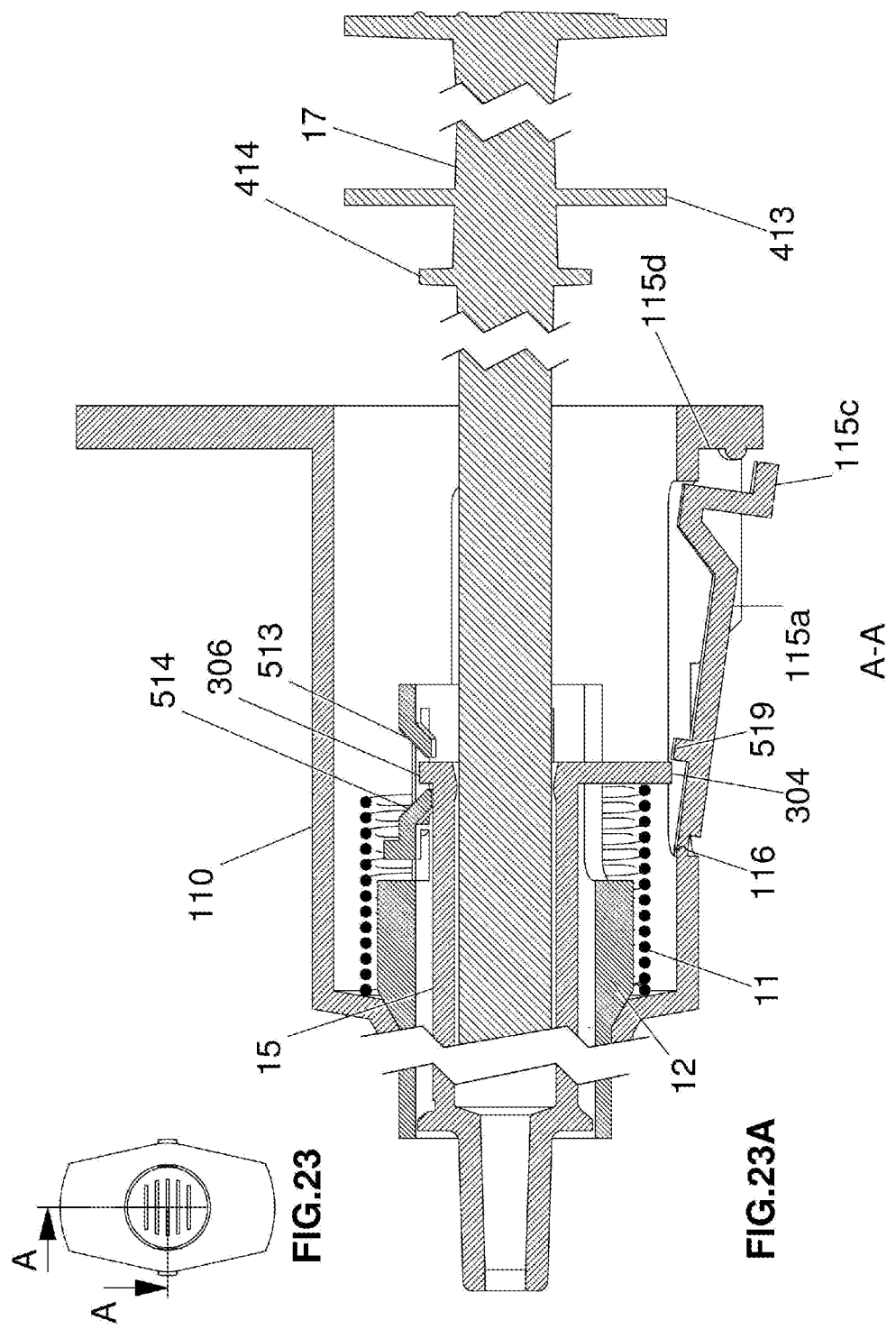

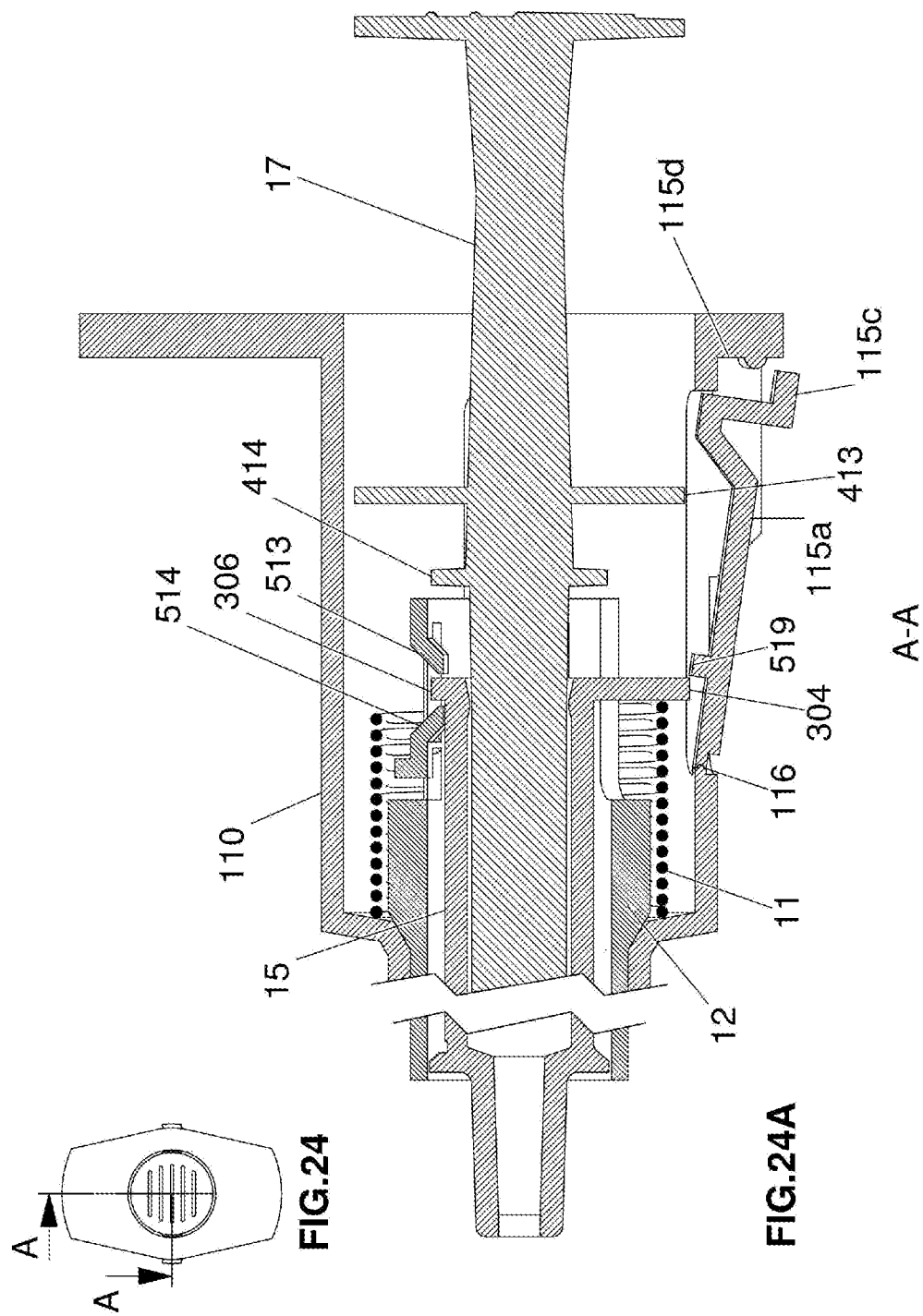

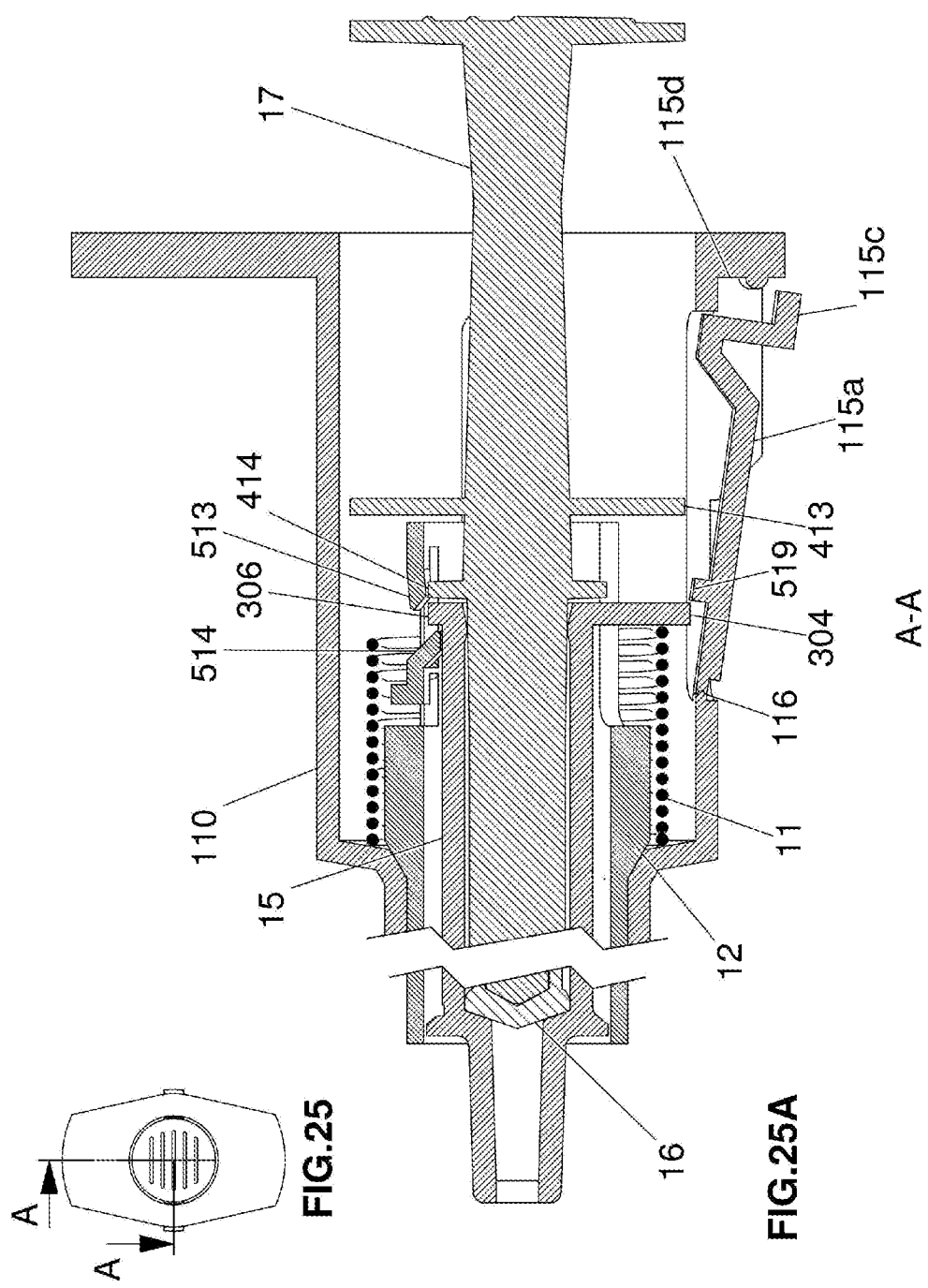

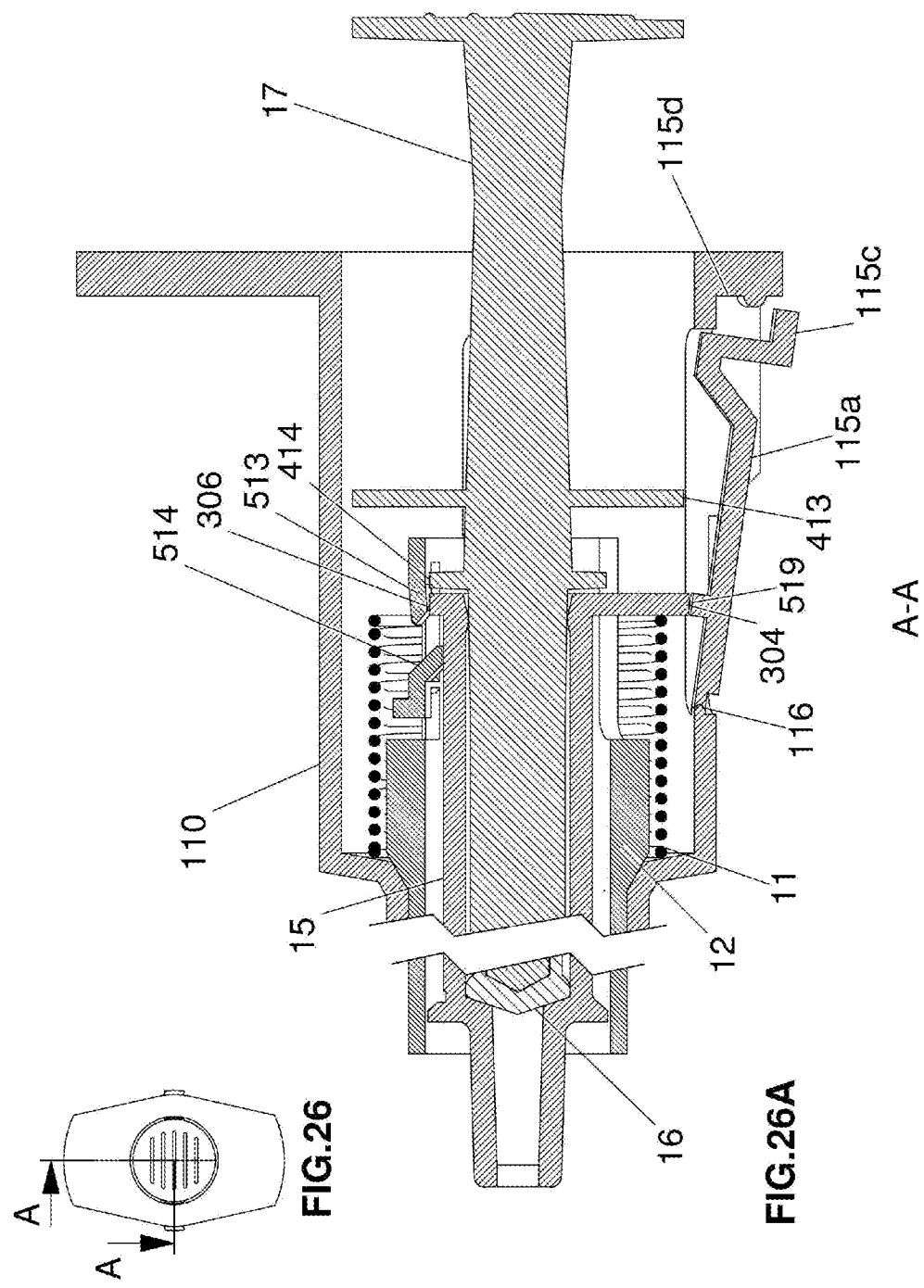

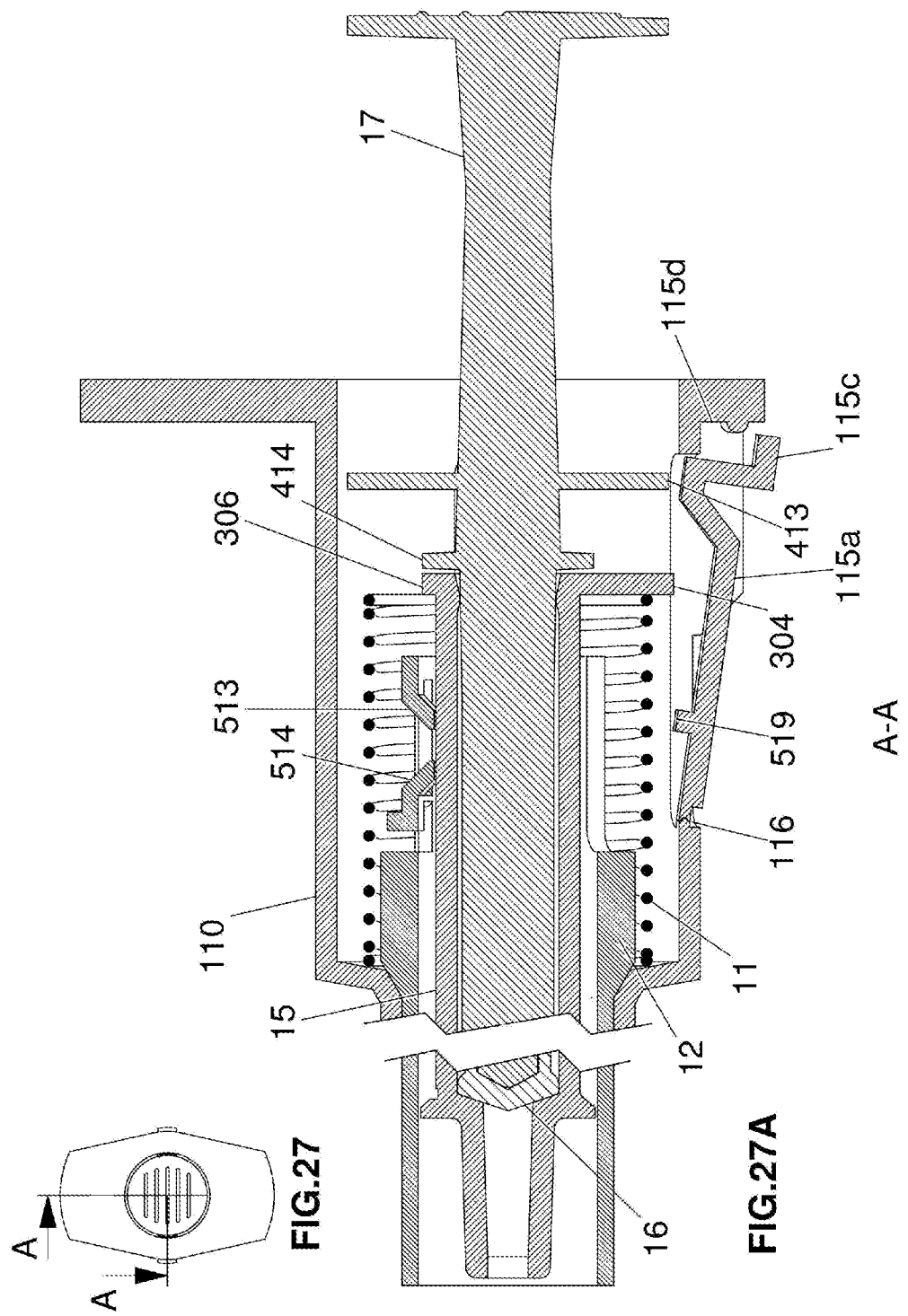

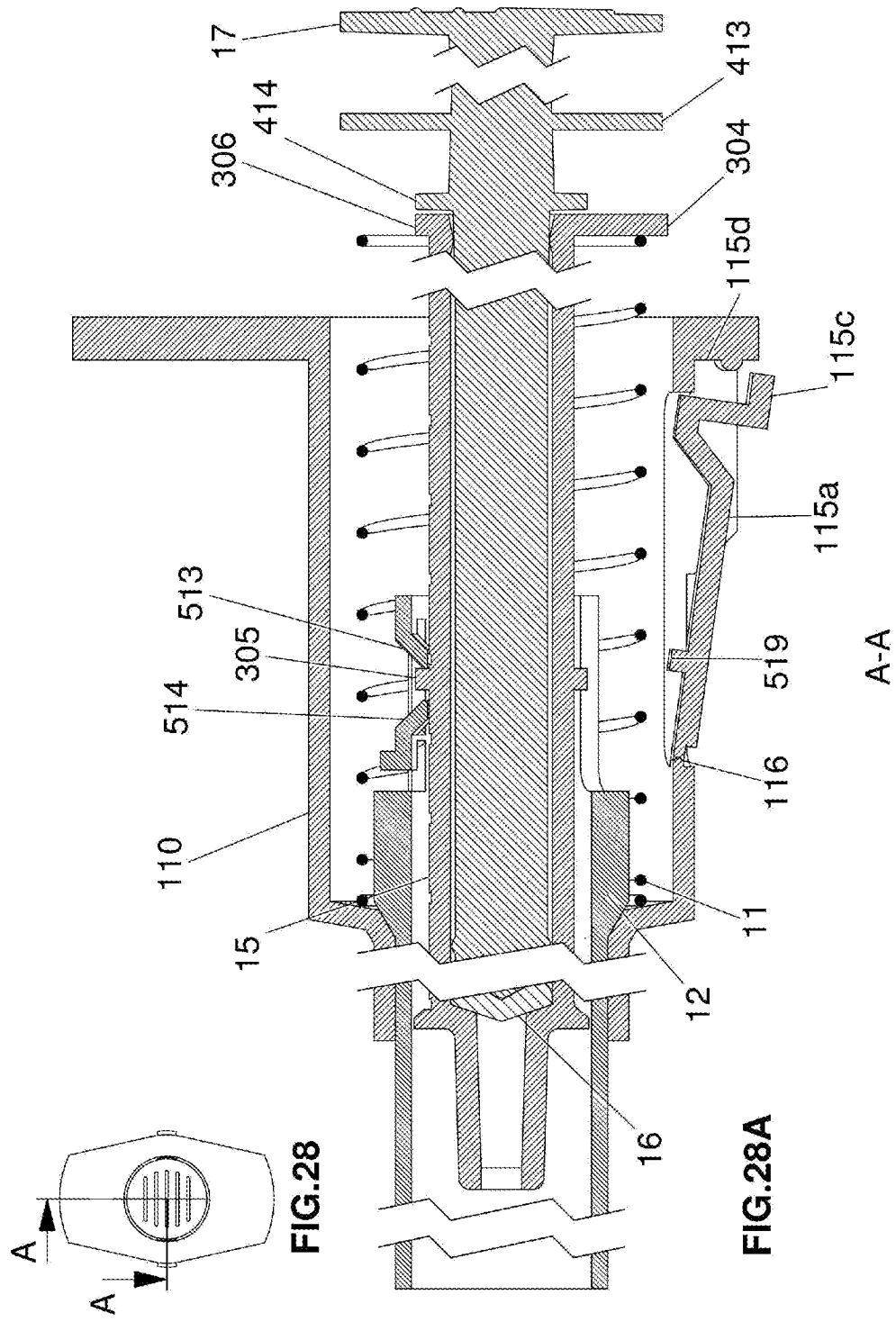

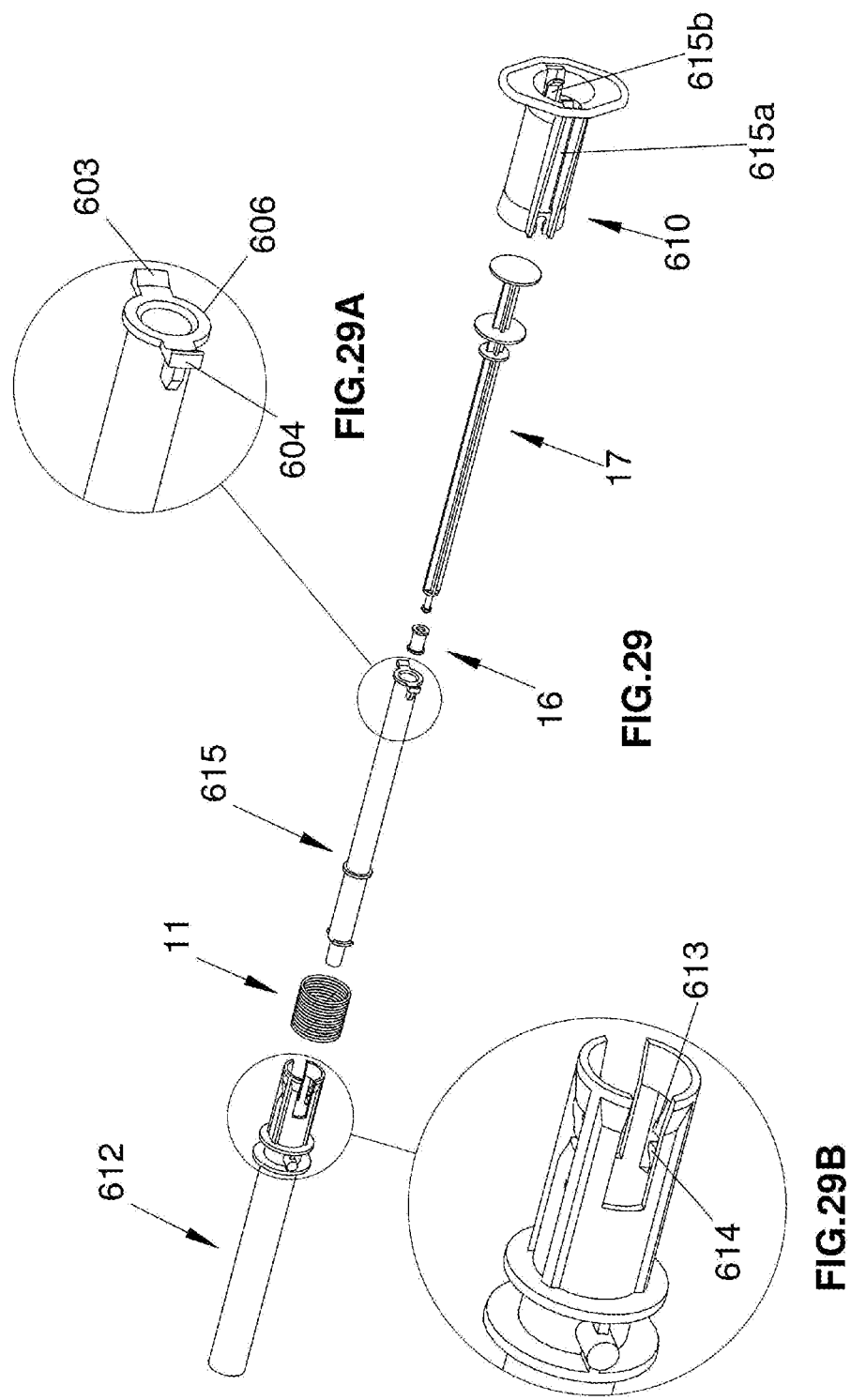

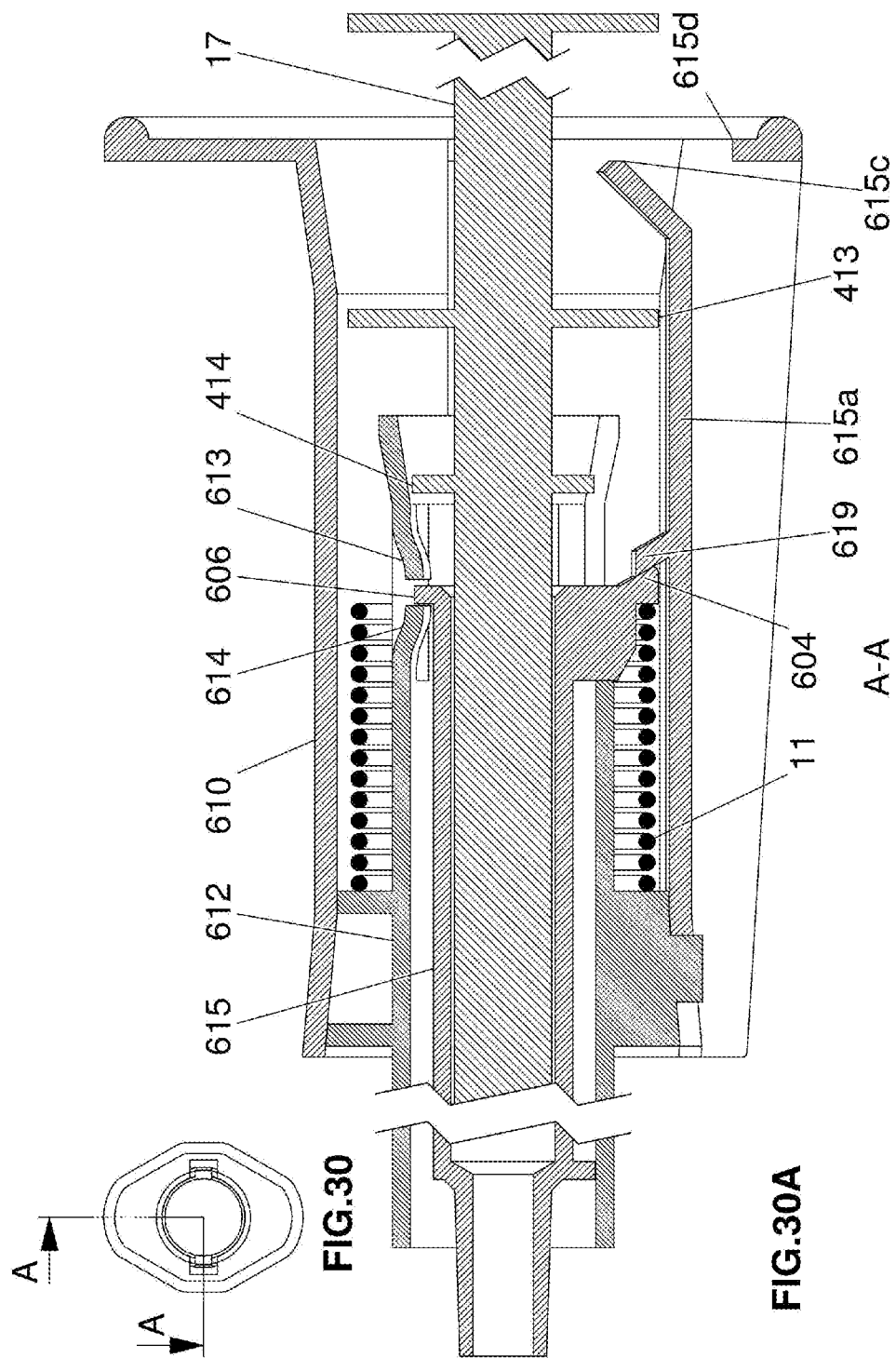

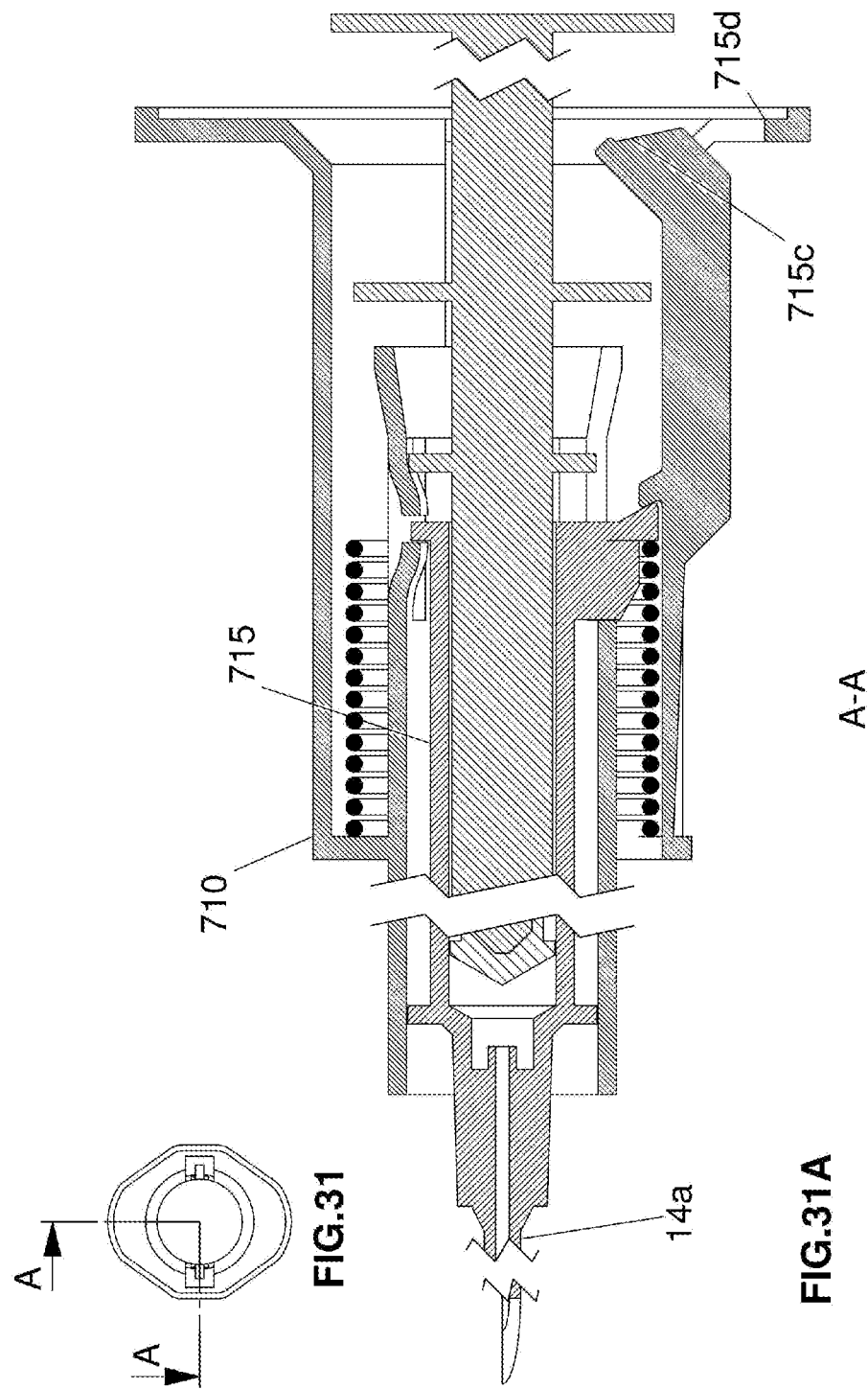

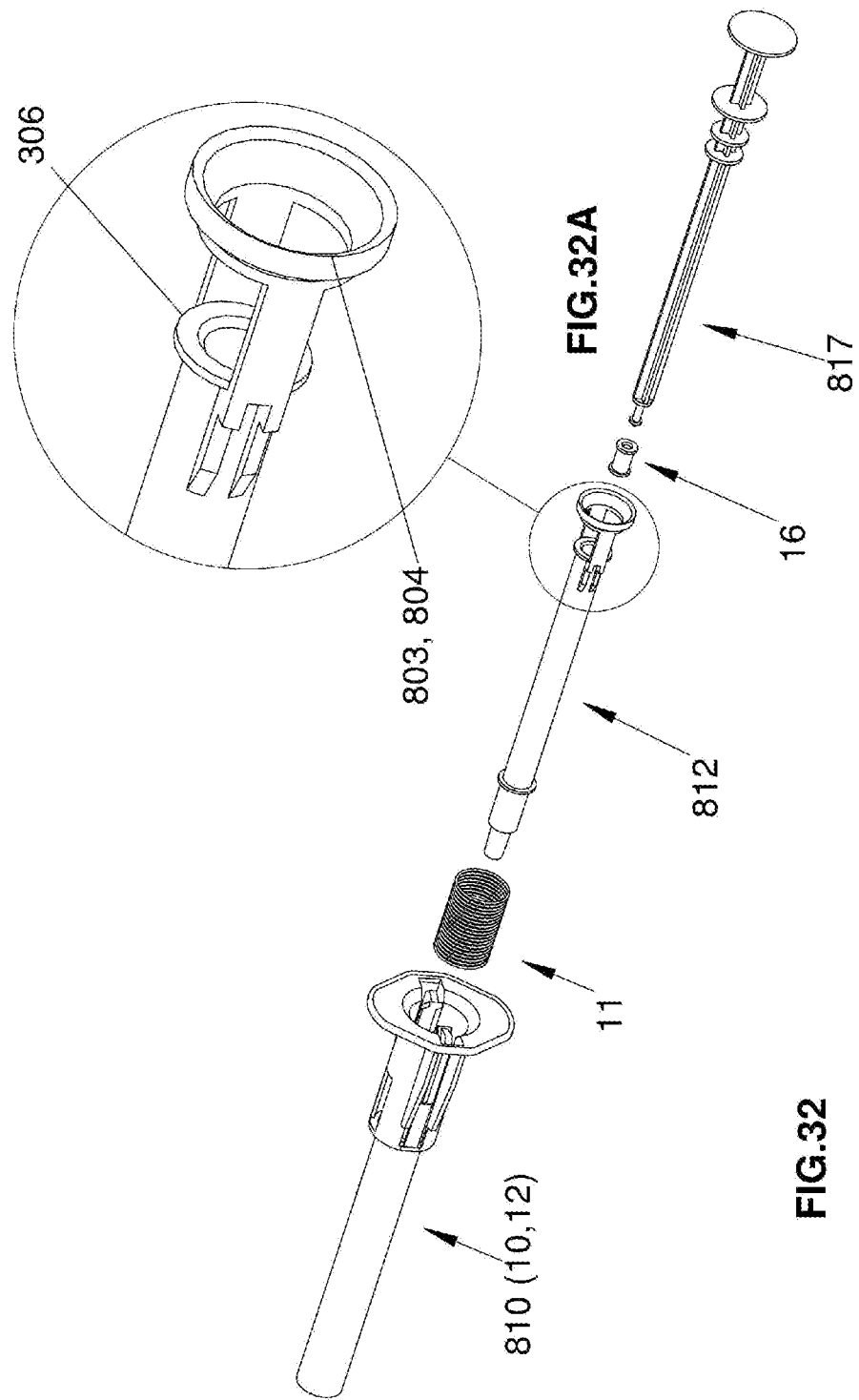

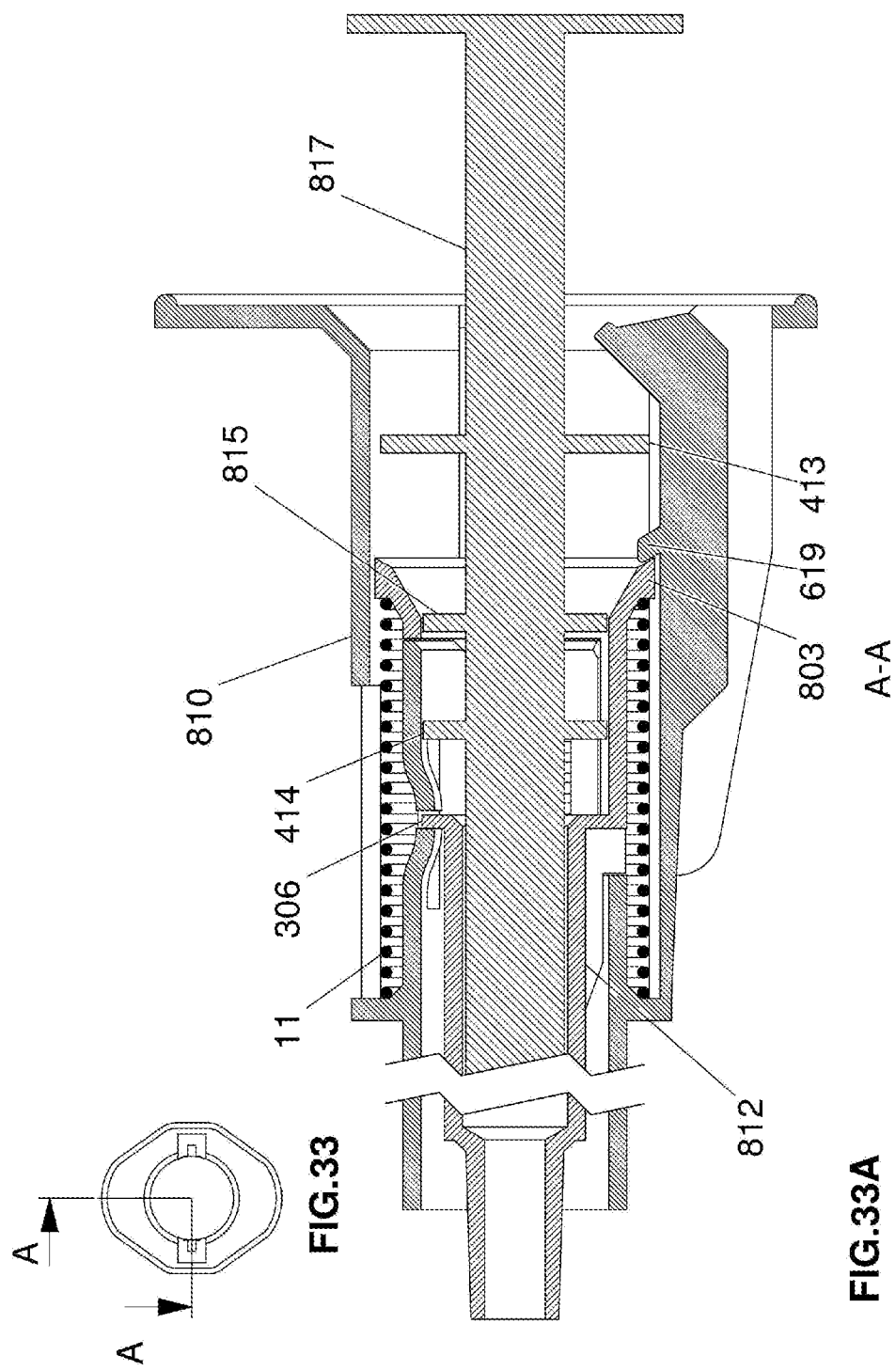

AUTO-RETRACTIBLE SYRINGE

BACKGROUND OF THE INVENTION

This invention relates in general to hypodermic syringes for manual injection and which have needles which auto-retract into a tubular component of the syringe known as an outer barrel after injecting a liquid dosage from an inner barrel and relates in particular to a hypodermic syringe with latch components for limiting or overriding latching movements of components prior to injection, during injection and needle retraction strokes corresponding to inward and outward movements of the syringe plunger.

SUMMARY OF THE INVENTION

The main object of the present invention is to provide a hypodermic syringe with a needle which retracts automatically after completion of dosage injection.

GENERAL DESCRIPTION OF THE INVENTION

The invention according to one aspect provides an auto-rectractible syringe which comprises; a housing, an inner barrel mounted and slidable within the housing, the inner barrel has means for mounting a needle unit thereon, or incorporates a needle; a plunger slidable within the inner barrel and with means thereon for withdrawing fluid comprising liquid dosage from a receptacle or collecting a biological specimen from a subject into the inner barrel when the plunger is drawn back and for injecting the dosage or expelling the collected biological specimen when the plunger is pushed forward, a spring adapted to exert retraction force against the inner barrel to retract the needle into the housing after usage, there being co-operating latching means formed on the plunger, the inner barrel and housing.

The housing includes axially-extending and radially-movable latching and unlatching hinged arms formed within and extending axially along the wall thereof and at the distal end thereof.

More specifically, each latching arm has formed on and depending from the inner surface thereof and intermediate the ends thereof, a pair of diametrically-opposed, latch members adapted to abut the proximal end of the inner barrel of the syringe when the inner barrel is in the needle-exposed position.

An additional latch member in the form of a rearwardly-sloped ramp is also formed on the inner surface of each latching arm and forwardly of to engage behind the flanged proximal end of the inner barrel to lock the inner barrel in locked position within the syringe housing.

The plunger has a solid shaft formed with a pair of axially-spaced and radially-extending latch-triggering discs thereon, there being a larger diameter and proximal-end disc and a smaller-diameter distal-end disc, the larger diameter and proximal-end disc being adapted to trigger primary latches formed by the latching hinged arms of the housing.

The invention also includes a method of operating a retractable syringe which has a housing, or outer barrel, an inner barrel, a plunger and a spring, the method comprises operating the plunger to activate latches formed on and between the housing or outer barrel and the inner barrel in a four-stroke cycle which comprises manually depressing the plunger in an inward/forward direction of air-expulsion first stroke, manually rearwardly withdrawing the plunger to initiate a dosage inward-drawing second stroke and trigger the first latch, manually, forwardly depressing the plunger in a dosage—injection, third stroke, whereby after completion of the injection third stroke by fully depressing the plunger, and releasing the second latch, the inner barrel and with it a hypodermic needle-carried by the inner barrel is automatically and rearwardly withdrawn by spring pressure into the outer barrel in a needle retraction fourth stroke, and at completion of the fourth stroke the inner barrel and with it the needle is retained in a fully-retracted rearward position by engagement of a third latch acting between inner and outer barrels.

In the method according to the invention, at least one latch retains the inner barrel in a forward and needle-exposed position and more specifically, the inner barrel is held by a plurality of latches in two positions namely a first or needle-advanced, needle exposed position and a second needle-retracted safe position.

In the method according to the invention after the final stroke, the inner barrel and with it the needle is retained in a fully-retracted rearward position within the housing by engagement of a third or locking latch acting between the inner barrel and the housing.

More specifically, in the method according to the invention rearward movement of the plunger and its associated discs precedes forward movement of the plunger to thereby release syringe latches and a partial rearward movement of the plunger partly releases the syringe latches.

Advantageous Features of the Invention

The trigger and latching mechanism components of the invention are mutually arranged and adapted to control the movement of the inner barrel, which is achieved by the configuration, placement and action of the first and second latches whereby once the first and second latches are disengaged by movement of the plunger, the inner barrel is moved backwards by spring pressure and applying pressure of a user's thumb on the plunger is able to limit the rate of rearward movement of the inner barrel.

A user can limit the rate of needle retraction and complete distal plunger travel can occur without triggering auto-retraction which thereby allows for inadvertent repeated distal plunger actions.

The inner barrel with a needle mount allows for choice of needle attachment and enables the changing of needles between drawing and dispensing a dose.

The invention allows a user to begin with a rearward stroke and omit an optional first air-expulsion stroke because the syringe will still be triggered for auto-retraction after an initial rearward stroke and subsequent full-forward stroke.

GENERAL DESCRIPTION OF THE DRAWINGS

A non-limiting embodiment of the invention will now be described with reference to the accompanying drawings in which FIG. 1 is an exploded perspective view of the components of one embodiment of a hypodermic syringe with auto-retracting needle according to the invention.

FIGS. 2 to 6 illustrate the collar component of the extended housing of the embodiment of the syringe shown in FIG. 1.

FIGS. 7 to 11 illustrate the outer barrel component of the housing of the embodiment of the syringe of FIG. 1.

FIGS. 12 to 16 illustrate the inner barrel component of the embodiment of the syringe of FIG. 1.

FIG. 17 is a perspective view of the plunger component of the syringe of the invention.

FIGS. 18 to 28 are sectional views of an assembled first embodiment of the syringe of invention taken through the collar and other syringe components showing internal structure of the syringe at its proximal end and illustrating both stationary and moving components and relative movements of associated co-operating latch and latch-triggering components.

FIGS. 18 to 28 are eleven sectional assembly views of a hypodermic syringe according to the first embodiment of the invention showing components in various relative positions from an initial as shipped mode to a final retraction mode after injection of dosage.

FIGS. 18 and 18A show the syringe in shipping mode for attachment of a needle on a needle mount.

FIGS. 19 and 19A show the syringe in expel air mode.

FIGS. 20 to 23A show the syringe in draw back mode.

FIGS. 24 to 25A show the syringe in dosage delivery mode.

FIGS. 26 to 28A show the syringe in retraction mode.

FIGS. 29 to 30A show a second embodiment of the syringe in shipping mode.

FIGS. 31 to 31A show a third embodiment of the syringe in shipping mode.

FIGS. 32 to 33A show a fourth embodiment of the syringe in shipping mode.

DETAILED DESCRIPTION OF THE DRAWINGS

Referring to the first embodiment of the invention shown in FIGS. 1 to 28A of the drawings and firstly to the exploded view of FIG. 1 there is shown-components of a hypodermic syringe for manual injection and which has a needle which retracts automatically into a hollow body of the syringe after completion of injection of dosage and which comprise; viewing from left to right, a collar 10 (more fully described later with respect to FIGS. 2 to 6 on Drawing Sheet 2); a needle-retraction coil spring 11 seated within a housing comprising a collar and an outer barrel 12, (more fully labelled in FIGS. 7 to 11 on Drawing Sheet 2), an inner barrel 15 (more fully labelled in FIGS. 12 to 16 on Drawing Sheet 3). A needle mount assembly 14 has a needle 14*a* in its mount 14*b*. The inner barrel 15 (shown in more detail and labelled 300 in FIG. 12 Sheet 4) has formed on its outer or away from user-facing distal end, a needle mounting lug 302 and latch-contacting external peripheral annular flanges labelled 303, 304, 305 and 306 are shown in FIG. 12 Sheet 4. A plunger 17 is shown at the right-hand side of the exploded view of the syringe componentry of FIG. 1 and in the assembly views of FIGS. 18 to 28A on Drawing Sheets 5 to 15. Referring again to FIG. 1 a piston 16 is adapted to be fitted to a lug 412 formed on the distal end of the plunger 17 which is formed with a solid shaft of cruciform section and a thumb pad 411 on its proximal end and which also has formed thereon and surrounding the shaft thereof a pair of axially-spaced, latch-triggering flanges comprising a larger diameter, user or proximal-end flange 413 and a smaller-diameter distal-end flange 414 as more clearly shown in the enlarged sequential views in the attached illustrations of FIGS. 18 to 33A on drawing Sheets 5 to 20. In FIG. 10A the outer barrel 12 has internally, diametrically-opposed latch members 223 and 224 formed therein which are adapted to be triggered by peripheral edges of a circular flange of the plunger.

Referring to the components of the exploded view of FIG. 1 on Drawing Sheet 1, there is shown a collar 10 which is also shown separately but re-numbered as 110 in FIG. 2 to 6 on Drawing Sheet 2, and in or through which other components of the syringe are placed or move. (When all syringe components are in an assembled "shipping" state this is shown in FIG. 18 of Drawing Sheet 5). The collar 110 is provided with a pair of primary latch members each on a primary latching and unlatching arm thereof formed in the wall of the collar, the movements of the primary or first latch arms are triggered by axial to and fro movements of the plunger 17 and with it two radial projections formed thereon which comprise a larger-diameter and axially proximally outermost disc 413 (FIG. 17 also on Sheet 1) which triggers primary latching and/or unlatching movements with respect to corresponding latch members on the collar 110 and inner barrel 15, respectively. Further corresponding latches are triggered by a smaller diameter and proximally innermost, radially-extending disc 414 (FIG. 17) formed on the plunger 17 engaging two inwardly facing resilient latch members 223 and 224 shown on FIGS. 7 to 11 on Drawing Sheet 3) on the proximal end of outer barrel 12 (200) and by latch member 306 (FIG. 12 Sheet 4) on an inner barrel 15, which are engaged and disengaged during the four-stroke cycle of air expulsion, dosage drawing, dosage injection and needle retraction. The collar 110 is formed as a hollow, stepped cylindrical body with a wider diameter or proximal end portion 111 shown in FIGS. 2 to 6 on Drawing Sheet 2 with an axial bore 112 extending therethrough which extends into a narrower-diameter distal-end portion 113 which also has an axial bore 112*a* extending therethrough. The wider-diameter body portion 111 of the collar has radially-outwardly directed finger grips 111*a* and 111*b* at the proximal end and a cylindrical wall 114 of the wider-diameter part has formed on either side thereof a pair of diametrically-opposite, axially-extending closed-off slots, such as the one in view labelled 115 in FIG. 4 of Drawing Sheet 2 and, extending axially along each closed slot is a latching arm 115*a* and 115*b* respectively, each arm being adapted to pivot radially-inwardly and outwardly in a limited arc in response to axial to and fro movements of the plunger, there being a pair of these diametrically opposed, latch-triggering arms, each being formed with a plastic hinge at one or distal end thereof, one such hinge 116 being shown in FIG. 5 (on Drawing Sheet 2), each latching arm 115*a* and 115*b* has formed thereon at the end opposite its hinge, a V-shaped-detent the base of which terminates in an axially-directed flat such the one labelled 115*c* each respective flat being adapted to alternatively engage within and be moved out of a shallow recess 115*d* formed behind each finger grip to control a latch mechanism formed between the arm and the edge of the proximal flanged end of the inner barrel when the latch triggering arm of the collar 110 is moved radially inwards and outwards by the larger-diameter outer or proximal flange of the plunger in association with rearward movement of the plunger 17 FIG. 1, now labelled 17(400), in FIG. 17 on Drawing Sheet 1 whenever the plunger 17 is manually withdrawn by a user and whenever triggered by two flanged latch triggering members comprising larger circular flange 413 of FIG. 18 on Drawing Sheet 5 or smaller flange 414 of FIG. 18, both flanges project radially outwards from the solid shaft 410 of the plunger 17 (400) near the distal end thereof as further shown by the sequential relative movements between component members in FIGS. 18 to 28A, In FIG. 3 of drawing Sheet 2 there is also shown two of four locating ramped axial flanges labelled 117 and 117*a*.

Referring to FIG. 7 toll on Sheet 3 of the accompanying drawings, the outer barrel 12 relabelled 200, has an open tubular in this case cylindrical body 212 with a tubular wall the user or inwardly-facing proximal edge of which is provided with two inwardly-opening axial slots 213 and 214 which open into the proximal (user-facing) edge of and extend partially into the outer barrel wall from the proximal edge. Opposed wall end sections located circumferentially between the two opposed proximal wall end slots 213 and 214 each have closed or internal and diametrically-opposed slots formed therein, there being two slots 215 and 216 respectively and located at each end of these internal slots there is formed a specially configured secondary latching member in the form of a downwardly and inwardly curved latching plate, there being a matching pair of axially-opposed latching plates 217 and 218 respectively. The top of each latching plate 217 and 218 has a radially outwardly projecting portion 219 and 220 respectively (see FIG. 10A) which extends above the curved exterior surface of the wall of the outer barrel 12(200), There is also formed on the outer barrel 12 a plurality of circumferentially equispaced alternating long and short external, axial ribs (in this example six) such the two short ones 221, 222 respectively as shown in FIG. 9.

Referring to FIGS. 12 to 16 on Drawing Sheet 4 of the accompanying drawings which show the inner barrel 15 of FIG. 1 on a larger scale, and renumbered 300. The inner barrel has an elongate open tubular and, in this case, cylindrical body 301 terminating at its distal end in a needle mounting lug 302, a pair of terminal and proximal winged flanges 303 and 304 which are adapted to fit within the pair of identical axial slots 213 and 214 at the proximal end of the outer barrel 12 in FIG. 1 now labelled 200 in FIGS. 7 to 10A. The outer surface of the tubular body of the inner barrel 15 (300), is provided with external peripheral flanges 305 and 308 and is provided with graduations such as the one labelled 307 shown respectively in FIGS. 12 to 16.

Referring to FIGS. 18 to 28A of Drawing Sheets 5 to 15, there is shown sequential movements of components during operation of the syringe. FIG. 18A shows relative positions of fixed and moving latching components in the initial stationary "As Shipped" first mode. FIG. 19A shows components of FIG. 18A moved to a second or "Expel Air" mode or first inward and forward stroke during which the plunger 17 is fully depressed. FIG. 20A (on Drawing Sheet 7), shows a second stroke movement wherein the plunger 17 is partly pulled out into a "Start Draw Dose" mode during which the smaller or second triggering disc 414 of plunger 17 has disengaged from the second latch 513 of the outer barrel. FIG. 21A shows relative positions of moving and stationary components during further outward or reverse movement of the plunger's second stroke in "Draw Dose and Start Trigger Latch" mode wherein the plunger 17 has been moved further outwards prior to engagement of its larger and outer disc 413 with latch arm 115a of the collar 110. FIG. 22A shows relative positions of components of FIG. 21A when in a "Draw Dose and Trigger Primary Latch" made of the second stroke. FIG. 23A shows relative positions of the discs two 413, 414 of plunger 17 and latch components when in an "End Draw Dose" mode at the end of the second stroke. FIG. 24A shows relative positions of plunger latch-triggering discs 413, 414 and latch components respectively when in a "Partially Expelled Dose" or in mid third stroke or injection mode. FIG. 25A shows the position of components of FIG. 24A when in "End Expelled Dose" or "Start Needle Retraction" mode at the beginning of the fourth and final stroke. FIGS. 26A and 27A show positions of components in partial needle retraction modes. FIG. 28A shows complete retraction with latching members 305, 513 and 514 engaged as the locking latch.

Referring to FIG. 18 on Sheet 5 of the drawings, there is shown in a sectional view of an assembled syringe in the ready-to-use shipping mode and which comprises a collar 110 (detailed in FIGS. 2 to 6) and which has formed in opposite sides of the wall thereof within a respective slot, elongate axially-extending members or primary latch-triggering arms 115a, 115b, one only of these being shown in FIG. 18 joined to the collar wall at one end via a plastic hinge 116 shown on FIG. 5 of Drawing Sheet 2 and again on FIG. 18 of Drawing Sheet 5. The opposite or free outer end of primary latch-triggering arm 115a is formed into a detent having an inwardly-facing V-shaped ramp one side of the base of which projects axially outwardly to form an end flat 115c which acts as a latch in association with a corresponding recess 115d formed in the rear surface of each respective finger grip 111a, 111b of the collar 10 when each latching arm 115a is constrained to move radially inwards or outwards in response to movements of the larger or proximal one 413 of two disc-like radial flanges formed on the plunger 17. The latching member 115a of the collar has a radially-inwardly facing internal latch component 519 formed thereon.

Referring to the inner barrel component 15 (300) shown in FIGS. 12 to 15 on Drawing Sheet 4, a first latching member 303 and 304 in the form of a larger-diameter external flanges are disposed adjacent the proximal end of the inner barrel 15(300). A second and smaller-radius latching member 306, in the form of an external flange is also formed on the proximal end of the inner barrel 15(300). A third latching member 305 in the form of a circumferential flange is formed on the inner barrel between the ends thereof.

FIGS. 29 to 30A show a second embodiment of the invention with different latching members. In FIG. 30A of the drawings the syringe comprises a housing collar portion 610 with axially-extending and radially-movable latching and unlatching hinged arms 615a, 615b formed within and extending axially along the wall thereof and at the proximal end thereof. Each latching arm has formed thereon and depending from the inner surface thereof and intermediate the ends thereof, a pair of diametrically-opposed, inclined latch members 619 (one only being shown in section), which are adapted to abut the proximal end of the inner barrel of the syringe when the inner barrel is in the needle-exposed position. FIGS. 29 to 30A also show alternative arrangements of; the outer barrel 612 and latch members 614 and 613; the inner barrel 615 and latching members 603, 604 and 606; and the collar 610 and latching arm members 615c and 615d.

FIGS. 31 and 31A show a third embodiment of the invention. In FIG. 31A the housing 710 is shown as a collar and outer barrel moulded as a unit. In FIG. 31A the inner barrel 715 is shown with the needle mount and needle moulded as a unit. In FIG. 31A the latching arm is shown with alternative arrangements of the detent members 715c and 715d.

FIGS. 32 to 33A show a fourth embodiment of the invention, FIGS. 32 to 33A show the inner barrel 812 with latch member 306 offset axially to latch members 803/804; the housing 810 is shown as a collar (10) and outer barrel (12) moulded as a unit; and the plunger 817 is provided with an additional protrusion 815 that may be used as a guiding and/or latching member.

According to the invention, relative axial reciprocating movements take place between the inner barrel and the collar, but no relative movement takes place between the outer barrel and the collar which remains fixed to the outer barrel or vice versa.

Latch members according to the invention are interchangeable whereby any arrangement or combination of latch members can be used for the latches.

In one form of the invention, either or both the inner barrel and housing are provided with graduations and can be made of transparent or translucent material.

The claims defining the invention are as follows:

1. A syringe which comprises, a housing, an inner barrel mounted and slidable within the housing, the inner barrel having means thereon for mounting a needle unit thereon, or incorporates a needle; a plunger slidable within the inner barrel and with means thereon for withdrawing fluid comprising liquid dosage from a receptacle or collecting biological specimen from a subject into the inner barrel when the plunger is drawn back and for injecting the dosage or expelling the collected specimen when the plunger is pushed forward, a spring adapted to exert retraction force against the inner barrel to retract the needle into the housing after usage, there being co-operating latching means formed on the plunger, the inner barrel and the housing, wherein the co-operating latching means includes at least one primary or first-released latch in the form of at least one latching arm formed in a wall of the housing and a first flange formed on a shaft of the plunger, wherein the at least one primary or first-released latch holds the inner barrel in a needle-exposed position and which is triggered and unlatched by the flange upon rearward plunger motion.

2. The syringe according to claim 1, wherein the at least one latching arm comprises a hinge formed at a distal end thereof, the at least one latching arm extending axially along the wall of the housing adjacent a proximal end of the housing and being radially-movable.

3. The syringe according to claim 2, wherein each latching arm comprises a latch member formed as a rearwardly-sloped ramp formed on an inner surface thereof, each ramp comprising a base projecting axially outwardly to form an end flat which acts as a latch in association with a respective recess formed in a rear surface of a respective finger grip of a collar of the housing.

4. The syringe according to claim 3, wherein the rearward plunger motion causes engagement of the flange with the rearwardly-sloped ramp and unlatching of the end flat from the recess.

5. The syringe according to claim 1, wherein the at least one primary or first-released latch formed along the wall of the housing comprises a pair of diametrically opposed, radially-movable, hinged latching arms.

6. The syringe according to claim 5, wherein each latching arm has formed on and depending from an inner surface thereof and intermediate to ends thereof, a latch component adapted to abut a proximal end of the inner barrel of the syringe when the inner barrel is in the needle-exposed position.

7. The syringe according to claim 1, wherein the shaft of the plunger comprises a distal end, a radially-extending, latch-triggering second flange formed thereon of smaller diameter than, and axially-spaced from the first flange.

8. The syringe according to claim 7, wherein the latch-triggering second flange triggers a latch formed in the housing after forward plunger motion and completion of delivery of the dosage or biological specimen from the syringe.

9. The syringe according to claim 8, wherein the latch is in the form of inwardly facing, diametrically opposed, resilient latch members formed in an outer barrel of the housing.

10. The syringe according to claim 1, wherein the housing has a proximal wall with a portion which is formed with at least one axially-extending, diametrically-opposed, closed off slot, the at least one slot enclosing the at least one latching arm which is hinged at one, distal end to a distal end wall of the closed off slot.

11. A method of operating a syringe which has a housing, an inner barrel mounted and slidable within the housing, a plunger slidable within the inner barrel for withdrawing fluid comprising liquid dosage from a receptacle or collecting biological specimen from a subject into the inner barrel when the plunger is drawn back and for injecting the dosage or expelling the collected specimen when the plunger is pushed forward, a needle mounted to the inner barrel and a spring adapted to exert retraction force against the inner barrel to retract the needle into the housing after usage, the method comprising operating the plunger to activate co-operating latches formed on the housing, the plunger and the inner barrel, wherein at least one primary or first-released latch in the form of at least one latching arm formed in a wall of the housing and a first flange formed on a shaft of the plunger holds the inner barrel in a needle-exposed position and operating the plunger comprises manually rearwardly withdrawing the plunger to activate a fluid withdrawing stroke and trigger and unlatch the at least one latching arm with the first flange.

12. The method according to claim 11, which includes an initial air-expulsion stroke by depressing the plunger in an inward/forward direction that does not trigger the primary or first-released latch.

13. The method according to claim 12, wherein a partial rearward movement of the plunger partly releases the at least one latching arm.

14. The method according to claim 11, further comprising manually forwardly depressing the plunger in a fluid-expelling stroke whereby after completion of the stroke by fully depressing the plunger, the inner barrel and with it the needle carried by the inner barrel is automatically and rearwardly withdrawn by spring pressure into the housing in a needle-retraction stroke.

15. The method according to claim 14, wherein the spring is disposed between a distal end of the inner barrel and a proximal end of the housing and the spring retracts the inner barrel and with it the needle completely into the housing after completion of delivery of the dosage or biological specimen from the syringe.

16. The method according to claim 14, wherein the inner barrel is held in a needle-retracted and safe position by engagement of a latching member formed on the inner barrel and latching members formed in an outer barrel of the housing.

17. The method according to claim 16, wherein the latching member is in the form of a circumferential flange formed on the inner barrel between ends of the inner barrel and the latching members are in the form of axially-opposed latching plates formed on the outer barrel.

18. The method according to claim 14, wherein rearward movement of the plunger and the first flange formed on a shaft of the plunger precedes forward movement of the plunger to thereby release the at least one latching arm.

19. The method according to claim 14, wherein a second latch is released by fully depressing the plunger.

20. The method according to claim 14, wherein at completion of the needle-retraction stroke, the inner barrel and with it the needle is locked in a fully-retracted rearward position by engagement of a third latch acting between the inner barrel and the housing.

\* \* \* \* \*